US005612539A

United States Patent [19]
Hoshi et al.

[11] Patent Number: 5,612,539
[45] Date of Patent: Mar. 18, 1997

[54] METHOD OF EVALUATING LIFETIME RELATED QUALITY OF SEMICONDUCTOR SURFACE

[75] Inventors: Ryoji Hoshi, Fukushima-ken; Yutaka Kitagawara, Takasaki; Takao Takenaka, Annaka, all of Japan

[73] Assignee: Shin-Etsu Handotai Co., Ltd., Tokyo, Japan

[21] Appl. No.: 557,563

[22] Filed: Nov. 14, 1995

[30] Foreign Application Priority Data

Nov. 14, 1994 [JP] Japan .................................. 6-279321

[51] Int. Cl.⁶ .................................................. G01R 31/265
[52] U.S. Cl. ................................................... 250/341.4
[58] Field of Search ........................................ 250/341.4

[56] References Cited

U.S. PATENT DOCUMENTS 4,652,757  3/1987  Carver ................................... 250/360.1

FOREIGN PATENT DOCUMENTS 6-132373  5/1994  Japan .................................. 250/341.4

Primary Examiner—Constantine Hannaher
Attorney, Agent, or Firm—Nikaido, Marmelstein, Murray & Oram LLP

[57] ABSTRACT

A lifetime related quality evaluation method, used with a semiconductor wafer having a semiconductor thin layer over the main surface of a semiconductor substrate, for evaluating the lifetime related quality of the semiconductor thin layer and/or the vicinity thereof, characterized by: generating electron-hole pairs in the vicinity of a surface of the semiconductor thin layer by the use of excitation light having a larger energy than the band gap of a semiconductor to be tested; then detecting the intensity at a particular wavelength of light emitted by recombination of the electron-hole pairs; and evaluating the lifetime related quality of the semiconductor thin layer and/or the vicinity thereof based on the detected intensity. The lifetime related quality evaluation method realizes a non-contact, non-destructive quality evaluation of the epitaxial semiconductor wafer.

16 Claims, 4 Drawing Sheets

METHOD OF EVALUATING LIFETIME RELATED QUALITY OF SEMICONDUCTOR SURFACE

BACKGROUND OF THE INVENTION

1. Field of the Invention

The present invention relates generally to lifetime related quality evaluation of a semiconductor surface, and more particularly to a lifetime related quality evaluation method of a semiconductor surface of the type wherein a semiconductor wafer having a semiconductor thin layer over the main surface of a semiconductor substrate is evaluated for the lifetime related quality (or information) of the semiconductor thin layer and/or the vicinity thereof to achieve a non-contact, non-destructive quality evaluation of the semiconductor surface.

2. Description of the Related Art

A semiconductor device is formed on, or in the vicinity of, the surface of a semiconductor material (silicon, for example). In recent years, the production of high-density, semiconductor devices has promoted the demand for a wafer having an epitaxial structure (hereinafter referred to as "epitaxial wafer") to improve the defect-free characteristics of the surface layer.

In parallel with the progress of the high-density trend of the semiconductor devices, a further reduction of the thickness or thinning of the semiconductor surface layer has been promoted, which will require quality evaluation of the thin surface layer with higher accuracy. Several techniques of evaluating the quality of semiconductor materials are known, which include the wafer lifetime method, the MOS C-t method, and the photoluminescence method.

In the conventional wafer lifetime method, an electromagnetic wave is used to generate excited carriers in the wafer for subsequent detection of a transient phenomenon in which the excited carriers become ceased to exist. However, since the excited carriers are generated in a relatively deep area, a problem is that the quality evaluation of a semiconductor thin layer, such as one having the epitaxial structure, cannot be achieved.

Especially, in an epitaxial structure having a semiconductor substrate with a reduced resistivity to deal with a latch-up problem, i.e., an operation failure of semiconductor devices, majority carriers in the semiconductor substrate become extremely predominant with the result that the conventional wafer lifetime measurement cannot be achieved.

In the MOS C-t method, the surface of a semiconductor thin layer is oxidized to form an oxide film, followed by a process of forming a gate electrode to which is applied a gate voltage to form a depletion layer directly below the surface of the semiconductor thin layer for enabling detection of a transient phenomenon in which minority carriers are generated within the depletion layer.

This method, however, is a destructive inspection and hence wafers which have already inspected can not be used to actual device fabrication processes. Furthermore, a device and a process to be added to achieve evaluation render the evaluation by this method expensive and complicated in procedure.

Moreover, information obtained by this evaluation method is limited to one related to a region of the semiconductor thin layer having a depth of several μm from the surface. Now considering that the thickness of the semiconductor thin layer ranges from several μm to several tens μm, a problem arises in that the evaluation method might be deemed insufficient to the equality evaluation of the semiconductor thin layer, on one hand, and cannot achieve evaluation of the interface between the semiconductor thin layer and the semiconductor substrate, on the other hand.

In the photoluminescence method, evaluation can be achieved in a non-destructive, non-contact manner. However, it is not clear about a depth to which extent the band edge emission attained by this method (namely, the emission at a wavelength of approximately 1.15 μm at room temperature, as shown in FIG. 4) actually contains information.

Especially in the case of the wafers of the epitaxial structure, when the resistivity of the semiconductor thin layer is relatively low (not greater than 0.1 Ωcm), emission intensity is strong or high and hence can be evaluated in itself. However, when the resistivity of the semiconductor thin layer is relatively high (not smaller than 1 Ωcm), emission intensity is weak or low, and carriers generated within the semiconductor thin layer diffuse out into the semiconductor substrate and emit light therefrom. As a result, evaluation of the emitted light may contain information about the semiconductor substrate.

In the case where the resistivity of the semiconductor substrate is relatively high, a light emitting region becomes indefinite. Accordingly, it occurs likely that not only the quality of the semiconductor thin layer but also the quality of the semiconductor substrate are detected concurrently. Under these circumstances, evaluation with higher accuracy cannot be achieved.

SUMMARY OF THE INVENTION

With the foregoing drawbacks of the prior lifetime evaluation methods in view, an object of the present invention is to provide a lifetime related quality evaluation method which is capable of evaluating the lifetime related quality (or information) of a semiconductor thin layer and/or the vicinity thereof in a wafer of the epitaxial structure, thus realizing a non-contact, non-destructive quality evaluation of the wafer.

To attain the foregoing object, the lifetime related quality erevaluation method of the present invention is a method of evaluating the lifetime related quality of a semiconductor thin layer and/or in the vicinity thereof in a semiconductor wafer having the semiconductor thin layer over a semiconductor substrate, wherein the method is characterized by: generating electron-hole pairs in the vicinity of a surface of the semiconductor thin layer by the use of excitation light having a larger energy than the band gap of a semiconductor to be tested; detecting the intensity at a particular wavelength of light (photoluminescence) emitted by recombination of the electron-hole pairs; and evaluating the lifetime related quality of the semiconductor thin layer and/or the vicinity thereof based on the detected intensity.

In this evaluation method, the excitation light having a larger energy than the band gap of the semiconductor to be tested is applied to an epitaxial wafer surface to generate electron-hole pairs in the vicinity of the irradiated wafer surface, and among rays of light (photoluminescence) generated upon recombination of the electron-hole pairs, the intensity of the so-called band edge emission which is emission of light at a wavelength of about 1.15 μm at room temperature is detected (see FIG. 4) to relatively evaluate the lifetime related quality (or information) on the detected emission intensity.

Since the excitation light used in the photoluminescence method has a wavelength in the visible region and shorter than the excitation electromagnetic wave used in a conventional lifetime measurement, excited carriers are generated at a region shallower than the corresponding region in the conventional lifetime measuring method. It is therefore possible to obtain lifetime ralated quality (or information) which is sensitive to the vicinity of the irradiated wafer surface.

In this invention, proper selection of the wavelength of the aforesaid excitation light makes it possible to selectively change the depth of a region where the electron-hole pairs are generated. Accordingly, the semiconductor thin layer either alone or in combination with the interface of the semiconductor thin layer and the semiconductor substrate and further with the semiconductor substrate can be selectively subjected to lifetime related quality evaluation.

In the case where the semiconductor substrate is composed of a low resistivity crystal, the wafer lifetime related quality evaluation of the semiconductor thin layer can be achieved with high accuracy. The term "low resistivity" is used herein to refer to a range of resistivity not greater than $0.1$ $\Omega$cm.

The evaluation method of this invention can preferably be used in an evaluation of the lifetime related quality of semiconductor wafers, and more particularly silicon wafers.

In the room temperature photoluminescence (PL) method, electron-hole pairs (namely, carriers) generated in the vicinity of a wafer surface upon irradiation of the wafer surface with the excitation light beam diffuse into the inside of the wafer during which time the carriers emit light (which can be detected as band edge emission) and then disappear. In this instance, when the resistivity of the wafer is relatively high (not less than $1$ $\Omega$cm), the carrier diffusion distance becomes relatively long and the band edge emission intensity is low or weak, and alternatively when the wafer resistivity is relatively low (not greater than $0.1$ $\Omega$cm), the carrier diffusion distance is relatively short and the band edge emission intensity is high or strong.

In the case of an epitaxial wafer composed of a semiconductor substrate having a relatively high resistivity and a semiconductor thin layer of a comparable resistivity deposited over the substrate, carriers generated in the semiconductor thin layer diffuse out into the semiconductor substrate and emit light therefrom. Accordingly, it may be considered that the evaluation obtained should reflect the influence of the semiconductor substrate.

On the other hand, in the case of an epitaxial wafer having a relatively high resistivity semiconductor thin layer deposited over a relatively low resistivity semiconductor substrate (namely, the so-called "epitaxial wafer with latch-up protection"), there is provided a structure which is composed of a semiconductor substrate with high emission intensity and a semiconductor thin layer with low emission intensity deposited over the substrate. With this arrangement, since carriers generated in the semiconductor thin layer disappear as soon as they arrive at the semiconductor substrate, a region of band edge emission is limited to the semiconductor thin layer and/or the vicinity thereof. It is therefore possible to achieve evaluation essentially for the semiconductor thin layer.

By reducing the wavelength of the excitation light beam used, it is further possible to shallow the region where the excited carriers are generated. This makes it possible to achieve lifetime related quality evaluation with high sensitivity to information about the vicinity of the wafer surface.

FIG. 2 conceptually shows the relationship between the semiconductor thin layer of a latch-up protected epitaxial wafer and the band edge emission intensity plotted when the thickness of the semiconductor thin layer is gradually increased.

When the thickness of the semiconductor thin layer is 0 μm (namely, when the wafer is composed solely of a semiconductor substrate), emission caused is solely from the low resistivity substrate and hence the emission intensity is a maximum. As the thickness of the semiconductor thin layer increases, emission from the semiconductor substrate is unlikely to occur with the result that the emission intensity decreases progressively.

After the thickness of the semiconductor thin layer exceeds the thickness of the emission region, emission caused is solely from the semiconductor thin layer and hence the emission intensity becomes constant. The very thickness determined when the emission intensity becomes constant is deemed to be a minimum depth to which the band edge emission only from the semiconductor thin layer is contributive.

Accordingly, by finding out the minimum depth, a proper wavelength of the excitation light corresponding to the thickness of the semiconductor thin layer can be selected. This will ensure that lifetime related quality evaluation of the semiconductor thin layer of an epitaxial wafer can be achieved with improved accuracy.

The above and other objects, features and advantages of the present invention will become manifest to those versed in the art upon making reference to the detailed description and the accompanying sheets of drawings.

DETAILED DESCRIPTION OF THE INVENTION

The present invention will be described below in greater detail by way of the following examples which should be construed as illustrative rather than restrictive.

EXAMPLE 1

An experiment was made to find out the depth to which extent the band edge emission actually attained by the PL method contains information.

Figure 1:
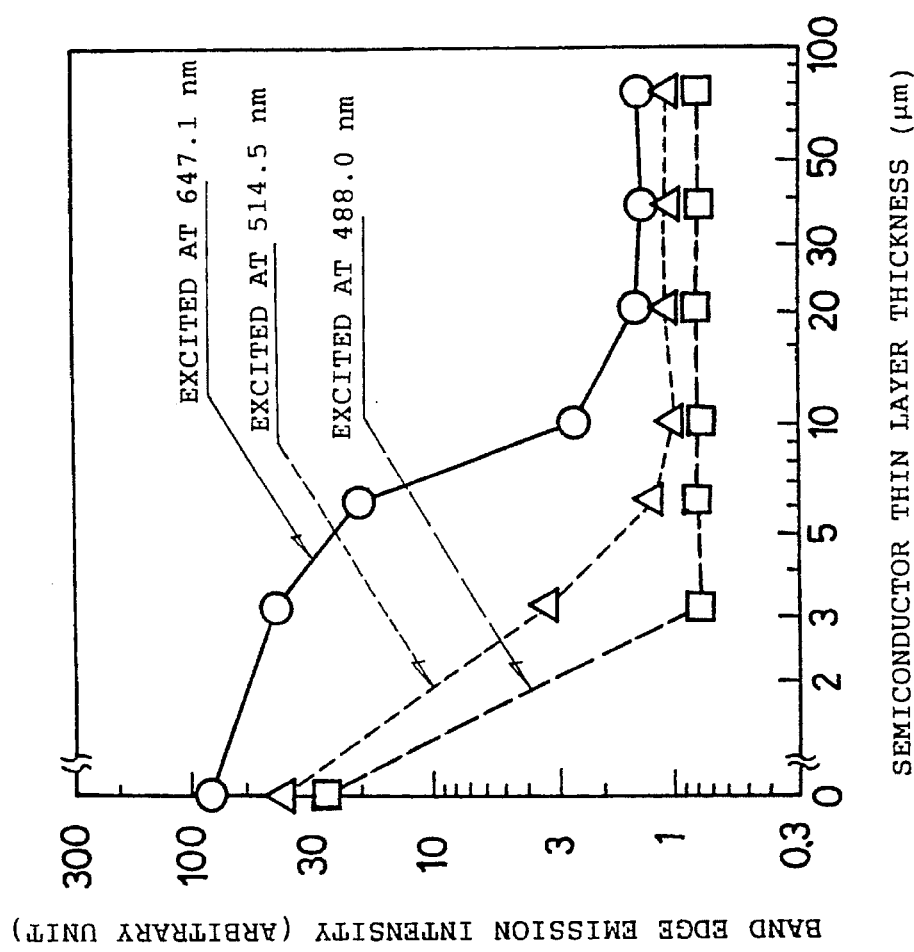
FIG. 1 is a graph showing the band edge emission intensity of photoluminescence in Example 1 in dependence upon the thickness of the semiconductor thin layer.
Figure 2:
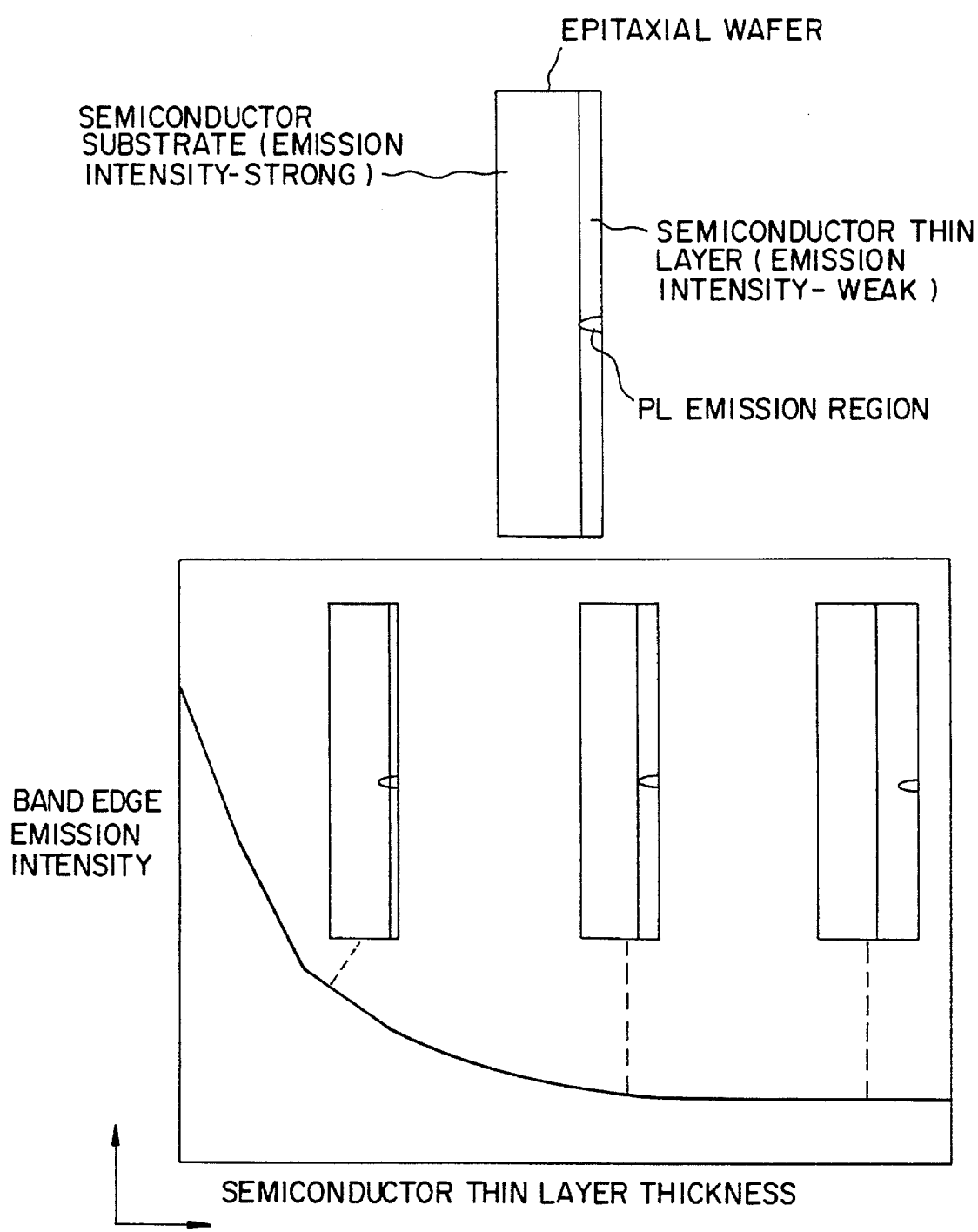
FIG. 2 is a diagrammatical view showing the relation between the thickness of the semiconductor thin layer and the band edge emission intensity.

Over a p-type low-resistivity ($0.017$ $\Omega$cm) silicon substrate, p-type $10$-$\Omega$cm semiconductor thin layers composed of an epitaxial silicon were deposited at various different thicknesses ranging from 0 to 80 μm to form an epitaxial wafer. The epitaxial wafer was tested for band edge emission intensity according to the room temperature PL method using an excitation light source having three different wavelengths, i.e., 647.1 nm, 514.5 nm and 488.0 nm. The result of this experiment is shown in FIG. 1.

The band edge emission intensity measurement was carried out under the following conditions.

Excitation beam diameter: 1 mmφ

Excitation light intensity: 200 mW (at laser head)

Laser plasma line removing filter: HA-30 (when excited at 647.1 nm and 488.0 nm) or bandpass filter (when excited at 514.5 nm)

Grating: 75 slits/mm with 2 μm breadth, slit width=2250 μm

Detector: Ge detector

It will be understood from FIG. 1 that when the wavelength of the excitation light is 647.1 nm, band edge emission intensities obtained with respect to those epitaxial silicon layers having thicknesses not greater than about 30 μm are high or strong and reflect information about the silicon substrate. When excited at 514.5 nm, high band edge emission intensities are obtained at the epitaxial silicon layers not greater than about 10 μm in thickness and reflect information about the silicon substrate. Similarly, when excited at 488.0 nm, band edge emission intensities are high at epitaxial silicon layers not greater than about 3 μm in thickness and reflect information about the silicon substrate.

Thus, in the case of the silicon substrate having a low resistivity such as 0.017 Ωcm, information related exclusively to an epitaxial silicon layer can be obtained by selecting a suitable wavelength of the excitation light beam according to the thickness of the epitaxial silicon layer. For epitaxial silicon layers having thicknesses not greater than 3 μm, the wavelength of excitation light used should be smaller than 488.8 nm.

EXAMPLE 2

It is known that heavy metal impurities cause degradation of the lifetime characteristics of silicon wafers. An epitaxial wafer having a p-type, 10-Ωcm semiconductor thin layer of epitaxial silicon deposited at 10 μm in thickness over a p-type low-resistivity (0.016 Ωcm) silicon substrate was intentionally contaminated with heavy metals, followed by a measurement of the lifetime characteristics of a surface layer according to the MOS C-t method. The measured lifetime characteristics was compared with the band edge emission intensity. The heavy metal impurity used for contamination purposes was iron, and the concentration of iron in a contamination solution was changed from 0 to 100 ppb.

The measurement was carried out under the following conditions.

1) Room temperature PL measurement:

Wavelength of excitation light source: 488.0 nm

Excitation beam diameter: 1 mmφ

Excitation light intensity: 200 mW (at laser head)

Laser plasma line removing filter: HA-30

Grating: 75 slits/mm with 2 m breadth, slit width=2250 m

Detector: Ge detector

2) MOS C-t measurement:

Oxide film: 50 nm

Gate electrode area: 0.0044 cm$^2$

Applied voltage: from −10 V to +10 V

Figure 3:
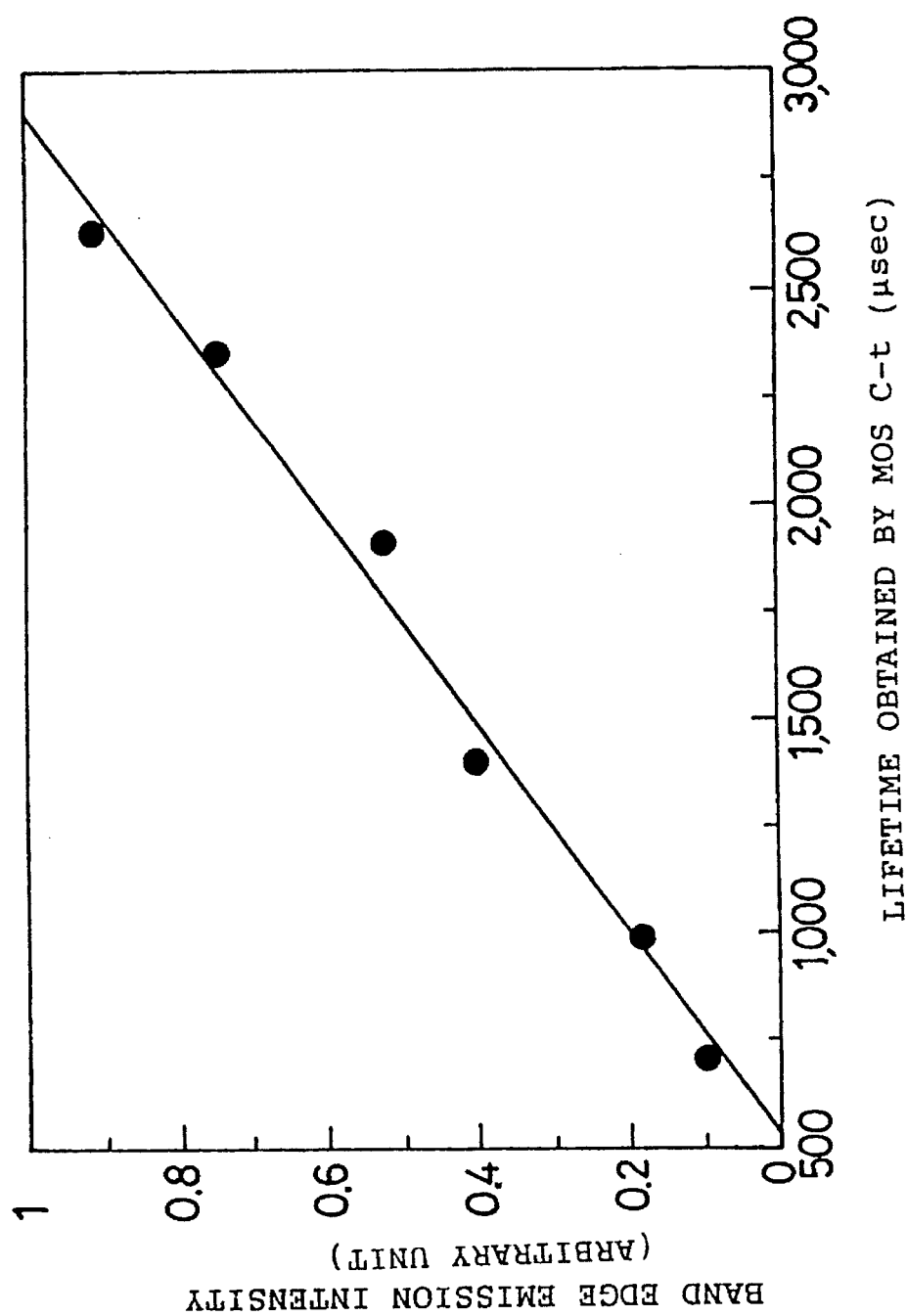
FIG. 3 is a graph showing the correlation between the band edge emission intensity of photoluminescence in Example 2 and the lifetime value measured by the MOS C-t method.
Figure 4:
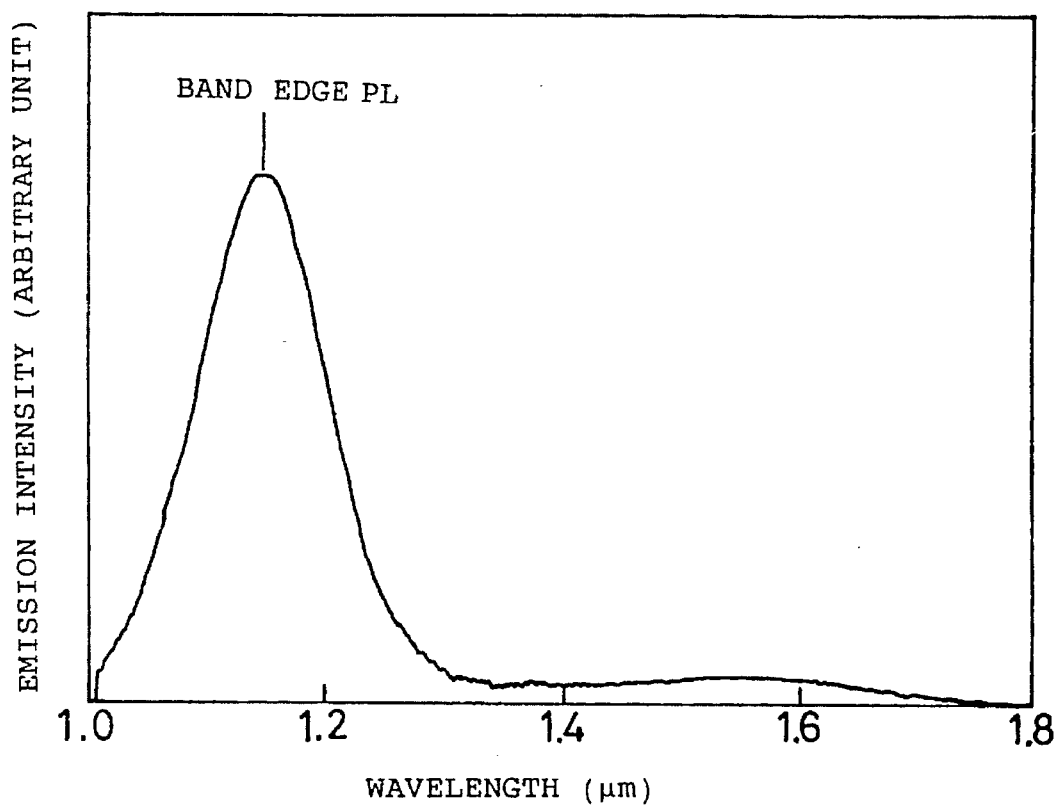
FIG. 4 is a view showing the emission spectrum of a silicon crystal attained by the room temperature photoluminescence.

FIG. 3 shows the correlation between measured values obtained by the room temperature PL measurement and those by the MOS C-t measurement. Since there is a good or close correlation between the measured values of the two lifetime measuring methods, it can be confirmed that the lifetime evaluation method of this invention reflects the lifetime characteristics of the semiconductor thin layer. The same correlation was also established when the excitation wavelength used was 514.5 nm. When the excitation wavelength was 647.1 nm, the correlation was somewhat weakened under the influence of the interface between the silicon substrate and the epitaxial silicon as compared with the case of the aforesaid two wavelengths, however, a certain degree of correlation was still established.

With an advance of the high integrality trend of the semiconductor devices, the need for a thinner layer has increased. According to the method of the present invention, such thinner layer can be evaluated by selecting an excitation light source of a shorter wavelength.

As is apparent from the Examples described above, information about the lifetime of a semiconductor thin layer alone and information of the lifetime of both the semiconductor thin layer and the substrate can be selectively obtained by properly selecting the wavelength of an excitation light source according to the thickness of the semiconductor thin layer.

As described above, the present invention successfully realizes a method which is capable of evaluating the lifetime related quality (or information) of a semiconductor thin layer which could never been evaluated conventionally. By selecting the wavelength of an excitation light source it is further possible to achieve evaluation of the interface between the semiconductor substrate and the semiconductor thin layer, and evaluation of the semiconductor substrate.

The room temperature PL method used in this invention can measure all samples as long as the surface condition of the samples is constant. This makes it possible to obviate the need for a surface treatment achieved in the conventional lifetime measuring method and the need for an electrode to be formed in the MOS C-t method, thus a fully non-destructive measurement being realized.

In sum, the method of the present invention is capable of achieving evaluation of the lifetime related quality (or information) of a semiconductor thin layer and/or the vicinity thereof in a wafer of the epitaxial structure, thus realizing a non-contact, non-destructive quality evaluation of the wafer.

Obviously, various minor changes and modifications of the present invention are possible in the light of the above teaching. It is therefore to be understood that within the scope of appended claims the invention may be practiced otherwise than as specifically described.

What is claimed is:

1. A method used with a semiconductor wafer having a semiconductor thin layer over the main surface of semiconductor substrate, for evaluating the lifetime related quality of the semiconductor thin layer and/or the vicinity thereof, said method comprising the steps of:

generating electron-hole pairs in the vicinity of a surface of the semiconductor thin layer by the use of excitation light having a larger energy than the band gap of a semiconductor to be tested;

detecting the intensity at a particular wavelength of light emitted by recombination of said electron-hole pairs; and evaluating the lifetime related quality of the semiconductor thin layer and/or the vicinity thereof based on the detected intensity.

2. A method according to claim 1, wherein said light emitted at said particular wavelength by recombination of said electron-hole pairs is band edge emission.

3. A method according to claim 2, wherein the wavelength of said excitation light is selected to selectively vary the depth of a region where the electron-hole pairs are generated, so that the semiconductor thin layer either alone or in combination with the interface of the semiconductor thin layer and the semiconductor substrate and further with the semiconductor substrate is selectively subjected to lifetime related quality evaluation.

4. A method according to claim 3, wherein the semiconductor substrate is composed of a crystal having a resistivity not greater than 0.1 $\Omega$cm.

5. A method according to claim 4, wherein said semiconductor wafer is composed of a silicon wafer.

6. A method according to claim 3, wherein said semiconductor wafer is composed of a silicon wafer.

7. A method according to claim 2, wherein the semiconductor substrate is composed of a crystal having a resistivity not greater than 0.1 $\Omega$cm.

8. A method according to claim 7, wherein said semiconductor wafer is composed of a silicon wafer.

9. A method according to claim 2, wherein said semiconductor wafer is composed of a silicon wafer.

10. A method according to claim 1, wherein the wavelength of said excitation light is selected to selectively vary the depth of a region where the electron-hole pairs are generated, so that the semiconductor thin layer either alone or in combination with the interface of the semiconductor thin layer and the semiconductor substrate and further with the semiconductor substrate is selectively subjected to lifetime related quality evaluation.

11. A method according to claim 10, wherein the semiconductor substrate is composed of a crystal having a resistivity not greater than 0.1 $\Omega$cm.

12. A method according to claim 11, wherein said semiconductor wafer is composed of a silicon wafer.

13. A method according to claim 10, wherein said semiconductor wafer is composed of a silicon wafer.

14. A method according to claim 1, wherein the semiconductor substrate is composed of a crystal having a resistivity not greater than 0.1 $\Omega$cm.

15. A method according to claim 14, wherein said semiconductor wafer is composed of a silicon wafer.

16. A method according to claim 1, wherein said semiconductor wafer is composed of a silicon wafer.

\* \* \* \* \*